(12) United States Patent
Canda

(10) Patent No.: US 7,996,240 B2
(45) Date of Patent: Aug. 9, 2011

(54) KNOWLEDGE-BASED SYSTEM FOR SUPPORTING RADIOLOGICAL ASSESSMENT AND DIAGNOSTICS

(75) Inventor: Valer Canda, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 636 days.

(21) Appl. No.: 12/033,949

(22) Filed: Feb. 20, 2008

(65) Prior Publication Data

US 2008/0201170 A1     Aug. 21, 2008

(30) Foreign Application Priority Data

Feb. 20, 2007   (DE) .......................... 10 2007 008 251

(51) Int. Cl.
*G06Q 10/00* (2006.01)
*G06Q 50/00* (2006.01)

(52) U.S. Cl. ............................... 705/2; 705/3; 382/128

(58) Field of Classification Search ............... 705/2–3; 382/128

See application file for complete search history.

(56) References Cited

U.S. PATENT DOCUMENTS

| 5,878,746 | A | 3/1999 | Lemelson et al. |
| 7,280,992 | B2 | 10/2007 | Nitz |
| 2005/0065814 | A1 | 3/2005 | Schmidt et al. |
| 2006/0242146 | A1 | 10/2006 | Piacsek et al. |
| 2008/0144939 | A1* | 6/2008 | Russakoff ..................... 382/190 |
| 2009/0094063 | A1* | 4/2009 | Ennett .............................. 705/3 |

FOREIGN PATENT DOCUMENTS

WO    WO 00/41613    7/2000

* cited by examiner

*Primary Examiner* — Luke Gilligan
(74) *Attorney, Agent, or Firm* — Schiff Hardin LLP

(57) ABSTRACT

In a method and a system for determination of at least one additional examination process in the framework of a medical examination of a patient using a knowledge base, the knowledge base contains a number of rules, and each rule contains a condition from which a result can be derived. An item of patient-related information is automatically registered and used to output the examination-specific result.

19 Claims, 1 Drawing Sheet

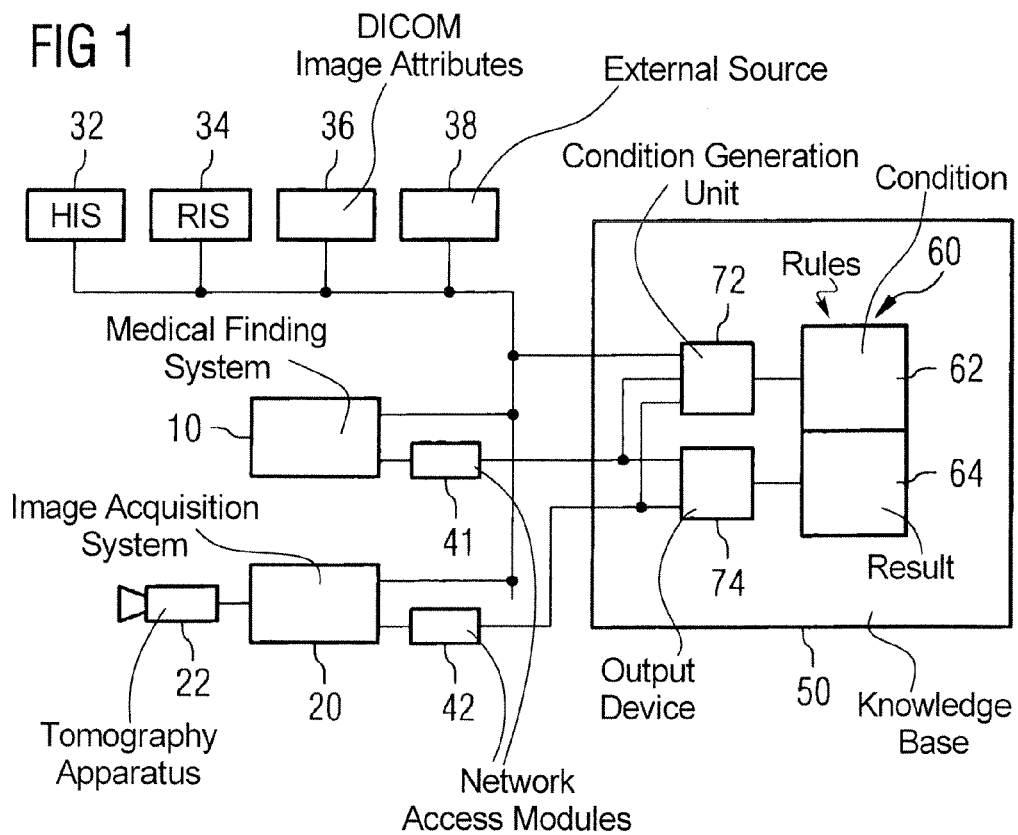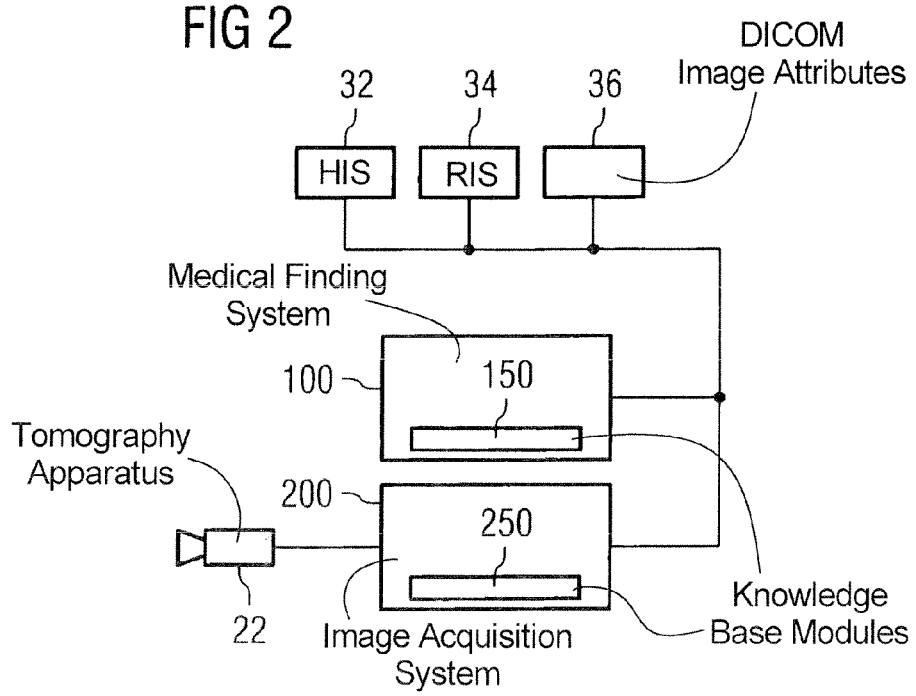

KNOWLEDGE-BASED SYSTEM FOR SUPPORTING RADIOLOGICAL ASSESSMENT AND DIAGNOSTICS

BACKGROUND OF THE INVENTION

1. Field of the Invention

The present invention concerns the field of medical examination apparatuses, and particularly in the field of radiological examination devices.

2. Description of the Prior Art

In the prevention, therapy and after-treatment of oncological illnesses, the search for new metastases is an important radiological object. In a whole-body metastasis examination, modern MR and CT tomography systems generate hundreds of slices images that the radiologist must search through for small lesions. In comparison to PET images in which malignant lesions occur with a very high contrast, such lesions can be relatively inconspicuous in MR and CT images. Due to the enormous quantities of images, for the physician the search is very laborious, tiring and thus also error-prone. In the worst case an error can have fatal consequences for the patient.

In order to minimize the risk of error, usually the so-called four-eyes principle is used. The assessing radiologist (frequently an assistant physician) examines the images, identifies possible occurring metastases and prepares a report. He or she discusses this report later with an experienced colleague (typically a senior physician) who looks at the most important images again. If the assessing radiologist has overlooked an inconspicuous metastasis, however, this may possibly still not be detected even in the second (quicker) check.

In order to minimize the risk of error, in some cases automated expert systems based on error trees are used for diagnostic support in medicine. Such an expert system directs the physician in the manner of a dialog system through a tree of decision points by means of questions and answers about examination results. The physician responds to individual questions (for example with regard to observed symptoms or examination results) and thus supplies the facts. The system then proceeds through the decision tree—from general knowledge to a specific diagnosis. Such a system helps the physician only in the diagnosis, and is strongly dependent on the inputs by the physician and is only conditionally suitable for error prevention. Such a system is known, for example, from DE 101 56 215 and from the corresponding published US application 2003/0092980.

DE 101 51 029 A1 and the corresponding published US application 2005/0065814 A1 describe an expert system in which the selection and order of the medical examination to be effected is automatically established using an expert system, starting from an initial diagnosis.

DE 10 2006 912 015 A1 and the corresponding published US application 2006/243146 A1 describe a system and a method for quantification of a selection property of an image volume which has been acquired by means of a medical imaging modality. An image section (for example a tumor) is thereby selected as representative and the variation of the image (and therewith of the tumor) is observed. Using a decision regulator, the variation can determine a diagnosis or a suggested course of treatment. The decision regulator can access a knowledge-based system (neural network) or a knowledge database.

WO 00/41613 describes a system for decision help in real time in medical treatment which accesses a knowledge-based expert system in order to output rational decisions and recommendations. The system analyzes input data about the health state of a patient and adapts these to rules of the knowledge base in order to arrive at conclusions. The knowledge base thereby also comprises a risk factor module in order to factor in health risks.

U.S. Pat. No. 5,876,746 describes a system in which, for diagnosis or treatment, medical examination results are compared with records of older examination results using a knowledge-based system in order to generate automatic suggestions for the continuative diagnosis. The use of the system is described with imaging examination methods such as CAT, PET, MRI or other radiological methods. The image data are analyzed with a feature extractor in order to make them compatible with rules of the database. A rule comprises a semantic assumption and a conclusion. Further commands can also be generated from the suggestions in order to execute further tests with the system.

Further minimization of the risk exists in optimally high-contrast and high-resolution acquisition methods, but these slower, more expensive and possibly more stressful for the patient.

A need therefore exists for a method and a system which devise the screening more simply and safely for the radiologist.

SUMMARY OF THE INVENTION

The present invention is a method for determination of at least one additional examination process in a medical examination of a patient using a knowledge base, wherein the knowledge base includes a number of rules, wherein each rule includes a condition from which a result can be derived, and wherein the result is correlated with the additional examination process. The method includes the steps of acquisition of at least one item of patient-related information, automatic generation of an examination-specific condition from the patient-related information, automatic determination of the examination-specific result belonging to the examination-specific condition to be generated using the knowledge base, and output of the examination-specific result, wherein the output of the examination-specific result contains at least one instruction with regard to an additional examination process and the instruction includes an instruction to implement further examinations, to observe further examination regions, to process image-related data and/or to display image-related data at an imaging device.

An "additional examination process" is any action that is relevant in the framework of a medical examination. It is typically an indication of further danger points or secondary lesions. The additional examination process can on the one hand be an act by a treating physician or medical personnel, for example the marking, examination or other treatment of lesions. The additional examination process can also be an examination with a medical examination or diagnosis device such as, for example, an imaging and/or radiological device, an acquisition system or an assessment (finding) system or the like.

The medical examination is generally an assessment or a diagnosis that can be executed with medical technology apparatuses.

According to the invention, the knowledge base is a collection (in particular a database) of rules. Each rule includes one condition (known as the If-part) and a result (known as the Then-part). The If-part can be one or more items of information about the patient and/or be information relevant or of interest to the patient. The information can also be designated as a fact.

A further object solution is to provide a device or a module that implements the method described above. The advantages, features and alternative embodiments that are mentioned above in connection with the inventive method are applicable to the inventive device, and vice versa.

The knowledge base can be a knowledge-based system. A knowledge-based system is an intelligent information system in which knowledge is mapped and made usable with methods of knowledge representation and knowledge modeling. Such a system is inventively used for error prevention and to increase the quality and safety of the medical finding.

According to the present invention, patient-related information are initially acquired. The acquisition can ensue by means of a text input into a data processing system, but can also be by access to a medical (in particular a radiological) examination system or other patient-related data. The data are then imported from an internal or external instance via special interfaces. The patient data can be stored on patient cards or in databases such as, for example, the HIS (Hospital Information System) and/or RIS (Radiology Information System) or also in the assessment software and be acquired starting from these.

The acquisition of the patient-specific information can ensue wholly automatically (importation via interfaces) or semi-automatically (with user interaction).

A condition (known as the If-part) of a rule is then inventively generated from the acquired information. All or portions of the acquired information can thereby be merged into a condition. Alternatively, that condition or those conditions of an existing set of rules that best match the acquired information (that is thus the most examination-specific for the medical examination) are alternatively selected.

The corresponding result is determined from the examination-specific condition so generated. The result can comprise one or more instructions that refer to the additional examination process. For example, these instructions can refer to suspected lesion locations in or on the body of the patient.

The result can be directly output. In the simplest case, it can be displayed or printed out, but it can also be output to a medical finding or diagnosis system with the result and the instructions contained therein being appropriate by processed further.

However, the result can also be processed into instructions and then be output in the form of one or more instructions in order to instruct medical personnel or a medical apparatus to implement a further process such as, for example, a further examination or a treatment.

The instruction or the result itself can be an instruction to implement further examinations, to observe further examination regions, to process or to display imaging data by means of an imaging device. The instructions or the result serve as a control variable for subsequent processes such as, for example, for a post-processing or for a display on the screen, etc.

The determination or the output of the result can ensue before, during or after an assessment or an examination of the patient.

The output of the examination-specific result can be an evaluation, in particular using predefinable risk classes. The evaluation can be contained in the result itself or the result can subsequently be supplied with the evaluation. The evaluation can assess, for example, and accordingly mark specific instructions as particularly important, less important or only as background information. It is understood that other evaluation methods are possible, for example by means of factors or percentile specifications.

The rules of the knowledge base or the knowledge bases can be modified, expanded or erased in the method. The system can be designed as a self-learning system (neural network).

The present invention also includes to a method for maintenance of a knowledge base for the determination of at least one additional examination process in the framework of a medical examination of a patient using the knowledge base, wherein the knowledge base includes a number of rules, wherein each rule includes a condition from which a result can be derived, and wherein the result is correlated with the additional examination process. This method includes the steps of registration of information used in a diagnosis, registration of additional examination processes initiated in connection with the diagnosis; generation of a (possibly modified or updated) maintained rule, wherein the registered information maps to the condition of the maintained rule and at least one of the registered examination processes maps to the at least one result of the maintained rule; and storage of the maintained rule in the knowledge base.

All or selected method steps advantageously ensue automatically. The method is executed for all or for selected rules of the knowledge base and triggered according to predefinable maintenance criteria. For example, it can be set that an updating of the rules is always triggered when a specific time interval has past (for example one work day).

An existing rule can be used as a basis for the generation of the rule to be maintained. The existing rule can thereby be replaced by the rule to be maintained. The rule to be maintained can run through a control process before the storage in the knowledge base.

It is also possible to provide a new business model that accesses the inventive method and provides a knowledge base with an "experience set" of rules and their updates.

The inventive embodiments of the method described in the preceding can also be fashioned as a computer program product, wherein the computer is prompted to implement the inventive method described above and its program code is executed by a processor.

The invention also extends to a storage medium that is designed for storage of the computer-implemented method described in the preceding and is readable by a computer.

Moreover, it is possible for individual components of the method described above to be executed in a commercial unit, for example as a module, and the remaining components can be executed in another commercial unit (as a distributed or integrated system).

BRIEF DESCRIPTION OF THE DRAWINGS

FIG. 1 illustrates a medical finding and acquisition system with an inventive system for determination of at least one additional examination process.

FIG. 2 illustrates a medical finding and acquisition system with an integrated inventive system for determination of at least one additional examination process.

DESCRIPTION OF THE PREFERRED EMBODIMENTS

In an embodiment shown in FIGS. 1 and 2 the present invention can extend a radiological examination system (such as a medical finding system 10, 100 and/or an image acquisition system 20, 200), with a system for determination of at least one additional examination process using a knowledge-base 50.

The acquisition system 20 or, respectively, the finding system 10 can have the form of a computer software (for example syngo that is commercially available from Siemens Healthcare) or an apparatus. The acquisition system 20 is connected with a tomography apparatus 22 that, for example, supplies MR or CT image data.

The system and method for determination of at least one additional examination process according to the invention should indicate (for example during an oncological examination, before or during the assessment) to the radiologist those body regions in which the occurrence of new lesions is possible or particularly probable based on the previous course of illness. Overlooking new lesions is thereby less probable.

In order to detect the endangered body regions, the system uses a knowledge base 50 in which the knowledge is stored (for example in the form of rules 60).

Such a knowledge base could be consolidated and maintained centrally, for example at the applicant (with the aid of medical experts).

As shown in FIG. 1, the knowledge base 50 can be located at a central location, for example at the applicant or another service provider. The knowledge base 50 can be accessed by a network by means of a module 41 attached to or integrated in the finding system 10 or, respectively, by means of a module 42 attached to or integrated in the acquisition system 20.

As shown in FIG. 2, the knowledge base 50 can also be integrated into the modules 150, 250. In this case the knowledge base can be use locally and therewith network-independent with the finding system 100 or the acquisition system 200. The modules 150, 250 can be retroactively added to the respective examination system 100, 200 or can be provided or distributed together with these systems.

A user can also have the possibility to extend his knowledge base with further knowledge, for example via addition of individual rules. Furthermore, the user should receive the possibility to acquire updates for his knowledge base 50 both from the central operator of the knowledge base and from other end users, for example to download said updates via the Internet or via another network.

In the framework of this invention it is therefore provided to offer a new business model in connection with an (in particular radiological) examination system. The inventive knowledge base 50 should be connectable to the examination system as a separate or integratable module.

The knowledge base 50 or the knowledge base system according to the described exemplary embodiment is based on rules 60 that each include at least one condition 62 (an If-part) and at least one result 64 (a Then-part).

Examples of rules are:
If DiagnosisText contains "prostate carcinoma", then AreasAtRisk+={"spinal column", "lymph nodes"}
If DiagnosisText contains "malignant melanoma", then AreasAtRisk+={"liver", "brain", "lymph nodes"}
If MainTumorBodyRegion=="thorax" and MainTumorLaterality=="left" and AreasAtRisk contains "lymph nodes", then ParticularlyAtRisk+="lymph nodes axila left"
If MainTumorBodyRegion=="thorax" and (PreviousMetastasesBodyRegions contains "thorax" or PreviousMetastasesBodyRegions contains "abdomen") and AreasAtRisk contains "liver", then ParticularlyAtRisk+="liver"

If applicable, a different knowledge representation than that in the form of rules would also be conceivable, for example in the form of a semantic network.

The condition thereby comprises one or more facts, i.e. information which are connected with the patient.

A patient-related information or, respectively, a fact is in this context a testable statement (for example, DiagnosisText contains "prostate carcinoma") that is checked in the If-part of a rule. New facts can arise from the initial facts by the application of the rules. The patient-related information does not necessarily have to be textual information, rather can be based on other data that are imported via an interface and possibly extracted from a further instance. For example, the patient-related information can be extracted from non-textual data fields that comprise relevant clinical information such as the following diagnostic codes: HCPCS, CPT, APC and/or ICD9 codes.

The inventive system can obtain its facts or patient-related information from a number of external sources, in particular:

from the HIS (hospital information system) 32 and RIS (radiology information system) 34, for example about the anamnesis, about symptoms, the previous course, texts of prior reports;

from the DICOM (digital imaging and communications in medicine) attributes 36 of the available images (for example body region, acquisition technique, contrast agent, patient weight);

from the acquisition system 20 and/or finding system 10 itself (for example number, position and sizes of the current lesions, active task flow, internal states and parameters of individual components, or an external source 88).

According to the invention, examination-specific conditions 62 are then generated from the collected facts in a condition generation unit 72. The condition generation unit 72 can be arranged in the knowledge base 50, as shown in FIG. 1. The condition generation can, however, also ensue in one of the modules 41, 42. In this case the facts are collected by the modules 41, 42 and the generated condition is communicated to the knowledge base 50.

As an alternative, however, the system itself can also recognize new rules and add them to the knowledge base, possibly only with the approval of the user. In an alternative embodiment, by statistical evaluation over a number of cases a self-learning system is used in order, for example, to detect that, in more than 80% of the previous cases in which the facts A, B and C were present, the user subsequently marked a suspect lesion in the liver. The system could, for example, derive the following new rule from this:

If A and B and C and liver→risk<80%, then liver→risk=80%.

For this the system can be extended with probability considerations, as described further below in detail.

A new quality of the knowledge base would be achievable with such an approach.

In a more complex embodiment of the invention—given corresponding networking and consent of the hospitals—the data or, respectively, observations that have been collected in a number of systems are relayed into a central statistical rule generation (for example at the applicant or at another central point). In comparison to a local system, the validity of such generated new realizations is higher by a multiple, possibly even comparable with clinical studies.

It can also be provided for the system task for new facts from the user. However, the system can also operate entirely automatically in the background or be selectively connected.

Aside from a simple binary consideration (at risk/not at risk), a probability consideration of the risks is also possible. Instead of
If AreasAtRisk contains "liver"
the following rule can be determined
If liver→risk>30% and instead of
  AreasAtRisk+={"liver"}
the following rule can be determined
  liver→risk=liver→risk*1.2.

In a further advantageous embodiment of the invention, the system is operated with a fuzzy logic approach, such that the consideration is differentiated somewhat and the system could render the risk conclusions more precisely for the user with a percentile value.

The inventive system or, respectively, method can be integratable into an existing radiological software, for example via modules or plug-ins 41, 42 or, respectively, 150, 250 or can interact with these in another manner. The interaction with the radiological software also enables internal information and states of an acquisition system 20 and/or the finding system 10 to be used for the formation of facts.

The knowledge-based system 50 can recognize further body regions or, respectively, organs at risk with the aid of comprehensive knowledge base and by means of automatically collected facts. These realizations are utilized in order to direct the radiologist to the at-risk points before or during the assessment by, for example, the result of the rule being output.

For this the inventive system can possess an output device 74 that extracts from the result 64 the indications of the at-risk points and relays them via the corresponding modules 41, 42 to the respective examination systems 10, 20, for example in order to instruct these to execute a process.

The output device 74 can be fashioned as an external instance that is connected to the system via a corresponding interface. It can also be integrated into the module 41, 42 so that the result 64 is interpreted at the module and is translated into an instruction for an additional examination process.

The system can also instruct the radiologist only after the assessment, and merely indicate the points that were recognized as at risk in which the radiologist has, however, not yet placed a lesion marker. The radiologist is thereby influenced less before the examination. The system can then, for example, act as a safety check at the end of or after an examination.

For example, the inventive system can also trigger the following actions in an imaging device to identify the at-risk body regions determined by means of the results: mark in color, display enlarged, render at high resolution, adapt with filters before processing or otherwise so that the finding for these regions can ensue particularly efficiently. For this purpose, the system could possibly also alter the order or parameterization of the planned finding steps or adapt the sorting and visualization of the data sets in a data browser.

The system could also use the knowledge base in order to proactively indicate further at-risk points, i.e. before the image acquisition. This would, for example, enable the MTA to acquire the body parts of interest with a higher resolution or with a contrast agent administration, wherein smaller lesions would also be more easily detectable.

The system could possibly automatically alter the measurement program, for example add an additional "machine induced" scan into the measurement program or implement an automatic parameter adaptation of an already-planned scan. This would in particular be well feasible given non-invasive acquisition methods such as MR.

The field of oncological is surely not the sole application possibility of the described knowledge-based system. Comparable systems can also be well used for other indications (for example in neurology or cardiology). Instead of indications of potential new metastasis formation, they could then deliver indications of, for example, possible calcifications, stenoses, hemorrhages, tissue atrophy, function disruptions or other irregularities to be expected.

The knowledge-based system can additionally be extended beyond the detection of the points at risk. Such an extended system, for example, could make suggestions of further tests, finding tools and examinations or, respectively, even optimal medication and therapy. Instead of the integration into the acquisition or finding software, in this case an integration into the HIS/RIS would be advantageous.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for determining at least one additional examination procedure in a medical examination of a patient, comprising the steps of:
  providing an electronic knowledge base comprising a number of computerized rules, each rule comprising a medical condition from which a medical result is derivable, with each medical result comprising an indication of a region of a patient to be examined in an examination procedure;
  from an examination of an initial region of a patient, acquiring at least one item of patient-related information;
  generating an examination-specific condition from the patient-related information;
  entering said examination-specific condition into a computerized processor and, from said processor, accessing said knowledge base and determining, from among said number of rules, a determined rule comprising a medical condition that most closely corresponds to said examination-specific condition;
  in said processor, automatically implementing the determined rule to derive an examination-specific result corresponding to the medical result of the determine rule; and
  emitting said examination-specific result as an output from the processor comprising an instruction to implement the medical procedure comprised in the determined rule to observe the examination region comprised in the determined rule that is different from said initial region.

2. A method as claimed in claim 1 comprising employing a database of a knowledge-based computerized system as said knowledge base.

3. A method as claimed in claim 1 comprising allowing modification, extension or erasure of said number of rules in said knowledge base.

4. A method as claimed in claim 1 comprising using said instruction in said output to implement said additional examination process by a procedure selected from the group consisting of modifying processing of data associated with said examination procedure, modifying representation of data associated with said examination procedure, automatically causing a medical device to implement a medical treatment, and automatically causing a medical device to implement a medical diagnosis.

5. A method as claimed in claim 1 comprising, employing, as said patient-related information, information resulting from an oncological examination of a subject.

6. A method as claimed in claim 5 comprising determining said examination-specific result and deriving said examination-specific result in a computer, and supplying said patient-related information to said computer from a source selected from the group consisting of an internal storage unit accessible by the computer, an external storage unit accessible by the computer, and a manually operable interface connected to the computer.

7. A method as claimed in claim 1 comprising including in said output an evaluation of said examination-specific result based on predetermined risk categories.

8. A method as claimed in claim 1 comprising executing an assessment of said medical examination of the patient, and providing said output at a time selected from the group consisting of before assessment of said medical examination and during assessment of said medical examination.

9. A method as claimed in claim 1 comprising generating said patient-related information by a procedure selected from the group consisting of automatically recording said patient-related information, semi-automatically recording said patient-related information, automatically deriving said patient-related information from a diagnosis text, importing said patient-related information from a stand-alone source of patient-related information, and importing said patient-related information via an interface.

10. A non-transitory computer-readable storage medium encoded with programming instructions for determining at least one additional examination procedure in a medical examination of a patient, said medium being loadable into a computerized system comprising an electronic knowledge base comprising a number of computerized rules, each rule comprising a medical condition from which a medical result is derivable, with each medical result comprising an indication of a region of a patient to be examined in an examination procedure said programming instructions causing said computerized system to:
receive at least one item of patient-related information acquired from an examination of an initial region of the patient;
generate an examination-specific condition from the patient-related information;
access said knowledge base and determine, from among said number of rules, a determined rule comprising a medical condition that most closely corresponds to said examination-specific condition;
implement the determined rule to derive an examination-specific result corresponding to the medical result of the determine rule; and
emit said examination-specific result as an output comprising an instruction to implement the medical procedure comprised in the determined rule to observe the examination region comprised in the determined rule that is different from said initial region.

11. A module for determining at least one additional examination procedure in a medical examination of a patient for use with an electronic knowledge base comprising a number of computerized rules, each rule comprising a medical condition from which a medical result is derivable, with each result comprising an indication of a region of a patient to be examined in an examination procedure, comprising:
an input to receive at least one item of patient-related information from an examination of an initial region of a patient;
a condition generator that generates an examination-specific condition from the patient-related information;
a computer that accesses said knowledge base and determines, from among said number of rules, a determined rule comprising a medical condition that most closely corresponds to said examination-specific condition, and that implements the determined rule to derive an examination-specific result from corresponding to the medical result of the determine rule and that emits said examination-specific result as an output comprising an instruction to implement the medical procedure comprised in the determined rule to observe the examination region comprised in the determined rule that is different from said initial region.

12. A module as claimed in claim 11 for use with a knowledge-based system containing said knowledge base as a database thereof, and said module comprising an interface configured to place said module in communication with said knowledge-based system via a network.

13. A module as claimed in claim 11 wherein said knowledge base is a database integrated into said module.

14. A module as claimed in claim 11 wherein said module is integrated into a medical diagnostic device.

15. A module as claimed in claim 14 wherein said medical diagnostic device is a radiological diagnostic device.

16. A system for determining at least one additional examination procedure in a medical examination of a patient, comprising:
an electronic knowledge base comprising a number of computerized rules, each rule comprising a medical condition from which a medical result is derivable, with each result comprising an indication of a region of a patient to be examined in an examination procedure;
an acquisition unit that acquires at least one item of patient-related information from an initial region of a patient;
a computer supplied with said patient-related information that generates an examination-specific condition from the patient-related information and that accesses said knowledge base and determines, from among said number of rules, a determined rule comprising a medical condition that most closely corresponds to said examination-specific condition, and that implements the determined rule to derive an examination-specific result corresponding to the medical result of the determine rule, and that emits said examination-specific result as an output comprising an instruction to implement the medical procedure comprised in the determined rule to observe the examination region comprised in the determined rule that is different from said initial region; and
a display device in communication with said computer that visually displays said output.

17. A system as claimed in claim 16 wherein said acquisition unit is a radiological examination device.

18. A system as claimed in claim 16 wherein said acquisition unit is a medical finding system.

19. A system as claimed in claim 16 wherein said patient-related information represent information resulting from an oncological examination of the patient, and wherein said examination-specific result comprises instructions indicating suspicious locations of lesions in the patient.

* * * * *